US00PP32114P3

(12) United States Plant Patent
Hobbs

(10) Patent No.: US PP32,114 P3
(45) Date of Patent: Aug. 25, 2020

(54) ***FORSYTHIA* PLANT NAMED 'MNICH01'**

(50) Latin Name: ***Forsythia* x *intermedia***
Varietal Denomination: MNICH01

(71) Applicant: MCCORKLE NURSERIES, INC., Dearing, GA (US)

(72) Inventor: Christine Hobbs, Dearing, GA (US)

(73) Assignee: McCorkle Nurseries, Inc., Dearing, GA (US)

( * ) Notice: Subject to any disclaimer, the term of this patent is extended or adjusted under 35 U.S.C. 154(b) by 0 days.

(21) Appl. No.: 16/602,790

(22) Filed: Dec. 3, 2019

(65) Prior Publication Data

US 2020/0128715 P1 Apr. 23, 2020

(51) Int. Cl.
*A01H 5/00* (2018.01)
*A01H 6/00* (2018.01)
*A01H 5/02* (2018.01)

(52) U.S. Cl.
USPC ..... Plt./230
CPC ..... *A01H 6/00* (2018.05); *A01H 5/02* (2013.01)

(58) Field of Classification Search
USPC ..... Plt./230
CPC ..... A01H 5/00
See application file for complete search history.

*Primary Examiner* — Annette H Para
(74) *Attorney, Agent, or Firm* — James R. Holm

(57) ABSTRACT

A new and distinct *Forsythia* plant named 'MNICH01' particularly distinguished by new foliage growth exhibiting solid yellow coloration, unique leaf margin variegation on maturing leaves, leaf margin variegation that extends the showy period of the plant beyond the spring flowering period, and reduced plant size providing more compact plant form when compared to other standard commercial *Forsythia* cultivars, as disclosed.

7 Drawing Sheets

Genus and species: *Forsythia* x *intermedia.*
Variety denomination: 'MNICH01'.

BACKGROUND OF THE NEW PLANT

The present invention comprises a new and distinct variety of *Forsythia* plant, botanically known as *Forsythia* x *intermedia*, and hereinafter referred to by the variety name 'MNICH01'. This new *Forsythia* plant was discovered in 1997 by the inventor as a single branch mutation of *Forsythia* plant 'Lynwood Gold' (unpatented) growing in a cultivated area of a residence located in Dearing, Ga. The branch mutation was selected by the inventor based on its unique variegated leaf pattern. The branch mutation was removed from the original plant in 1997 and planted and rooted in a non-publicly accessible area of a commercial greenhouse located in Dearing, Ga. The single branch mutation was grown and further propagated the following year by vegetative stem cuttings. Plants of the new *Forsythia* variety were further propagated, grown and evaluated over the next 17 years to determine the stability of the unique variegated leaf pattern. 'MNICH01' has been found to retain its distinctive characteristics and has been found to be stable and reproduce true-to-type through over six generations of asexual reproduction by vegetative stem cuttings.

Plant Breeders Rights for this variety have not been applied for. 'MNICH01' has not been made publicly available or sold anywhere in the world prior to the effective filing date of this application.

SUMMARY OF THE INVENTION

The new *Forsythia* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Forsythia* variety when grown under normal horticultural practices in Dearing, Ga. The combination of these characteristics distinguishes 'MNICH01' as a new and distinct variety of *Forsythia:*

1. New foliage growth exhibiting solid yellow coloration;
2. Unique leaf margin variegation on maturing leaves;
3. Leaf margin variegation that extends the showy period of the plant beyond the spring flowering period; and
4. Reduced plant size providing more compact plant form when compared to other standard commercial *Forsythia* cultivars.

DESCRIPTION OF THE PHOTOGRAPHS

This new *Forsythia* is illustrated by the accompanying photographs which show the overall plant habit including flowers and foliage of the plant. The colors shown are as true as can be reasonably obtained by conventional photographic procedures. The photographs are of 3 and 4-year-old plants grown in 2-gallon and 3-gallon containers in Dearing, Ga. The photographs were taken in February 2019, March 2019 and September 2019 in Dearing Ga. under natural light conditions. Colors in the photographs may differ slightly from the color values cited in the botanical description which accurately describes the colors of the new variety.

FIG. 1 shows the flower buds and new vegetative growth.
FIG. 2 shows flower orientation and the flower buds.
FIG. 3 shows a typical open flower.

DESCRIPTION OF THE NEW VARIETY

Figure 1:
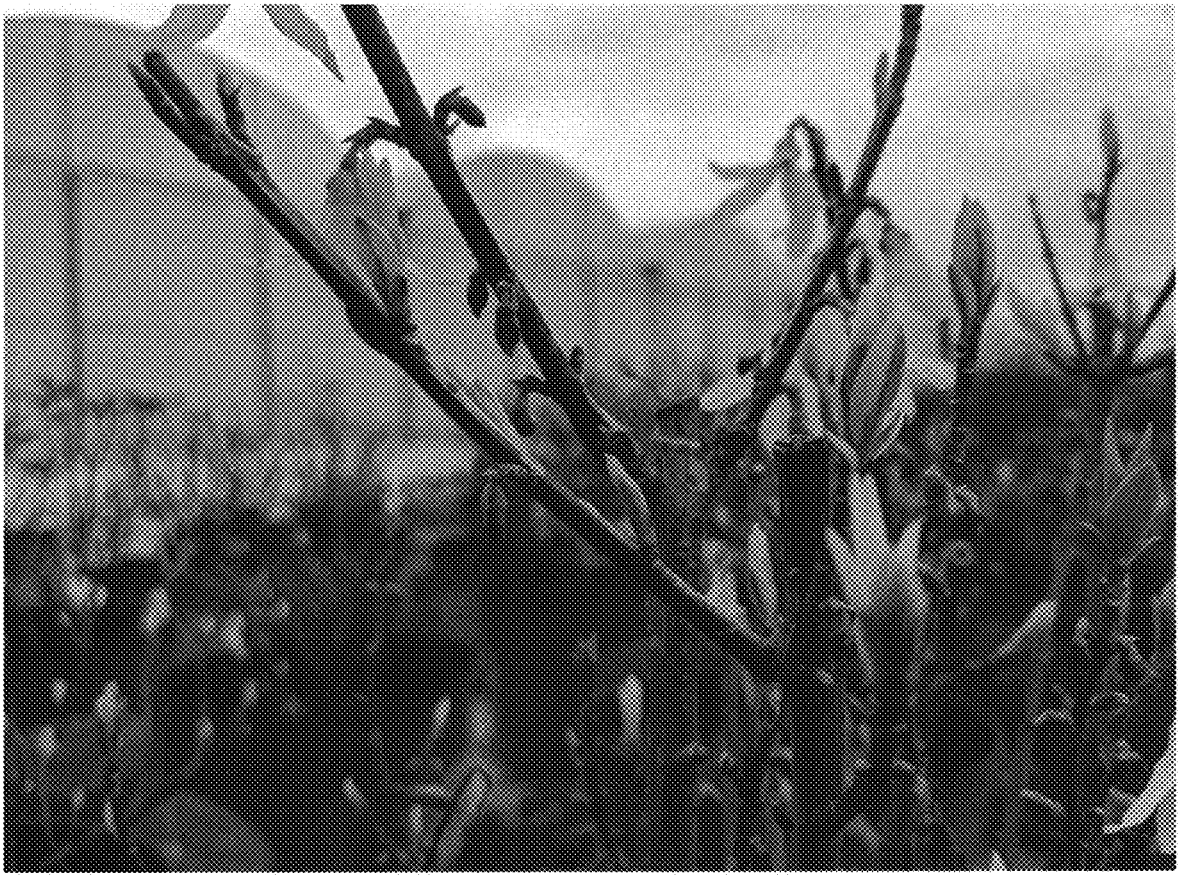
Figure 2:
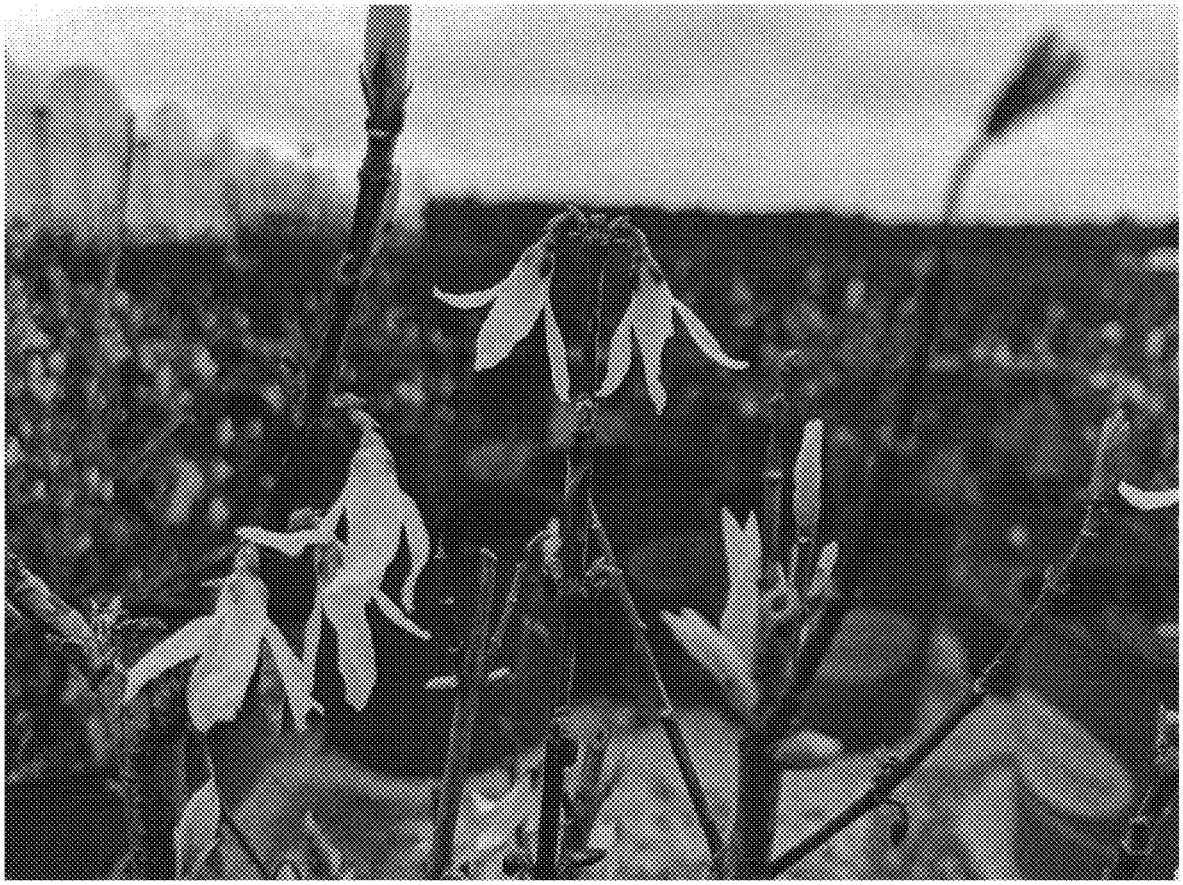
Figure 3:
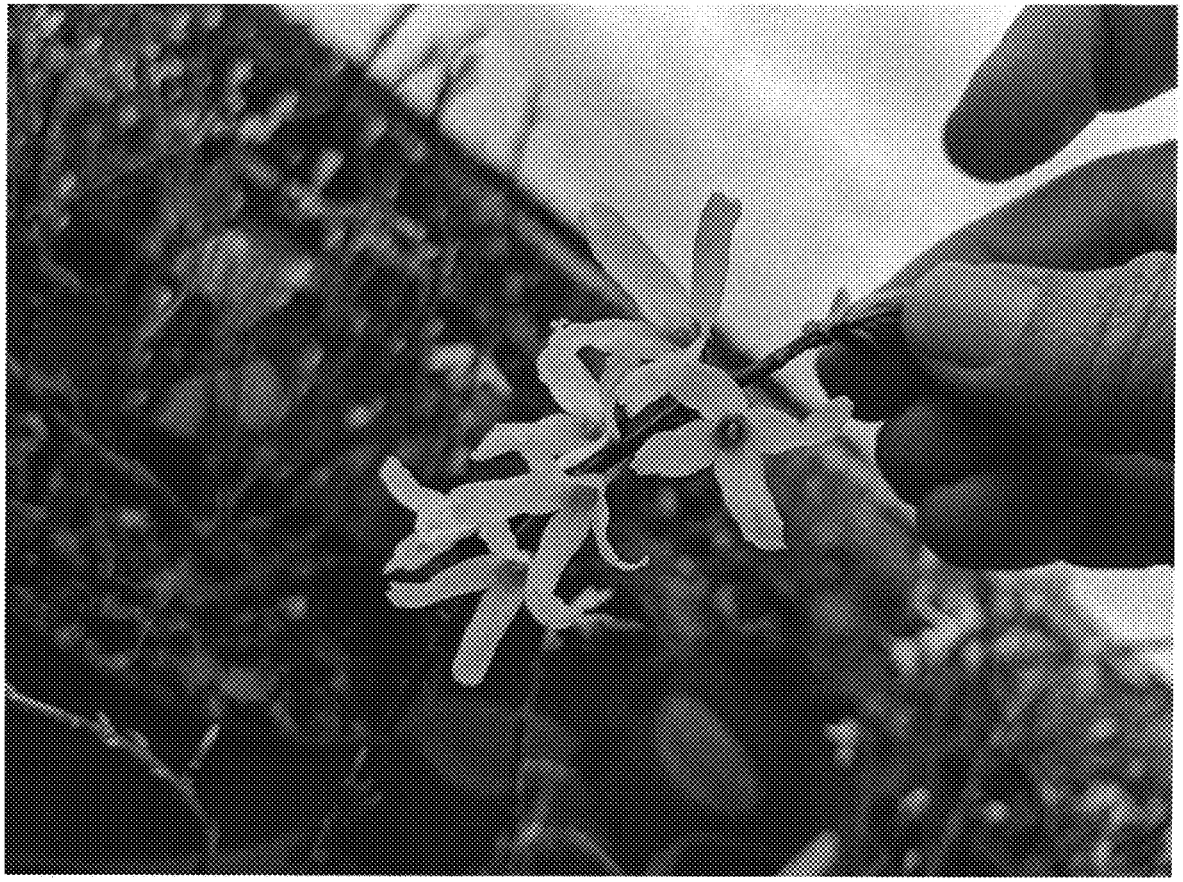
Figure 4:
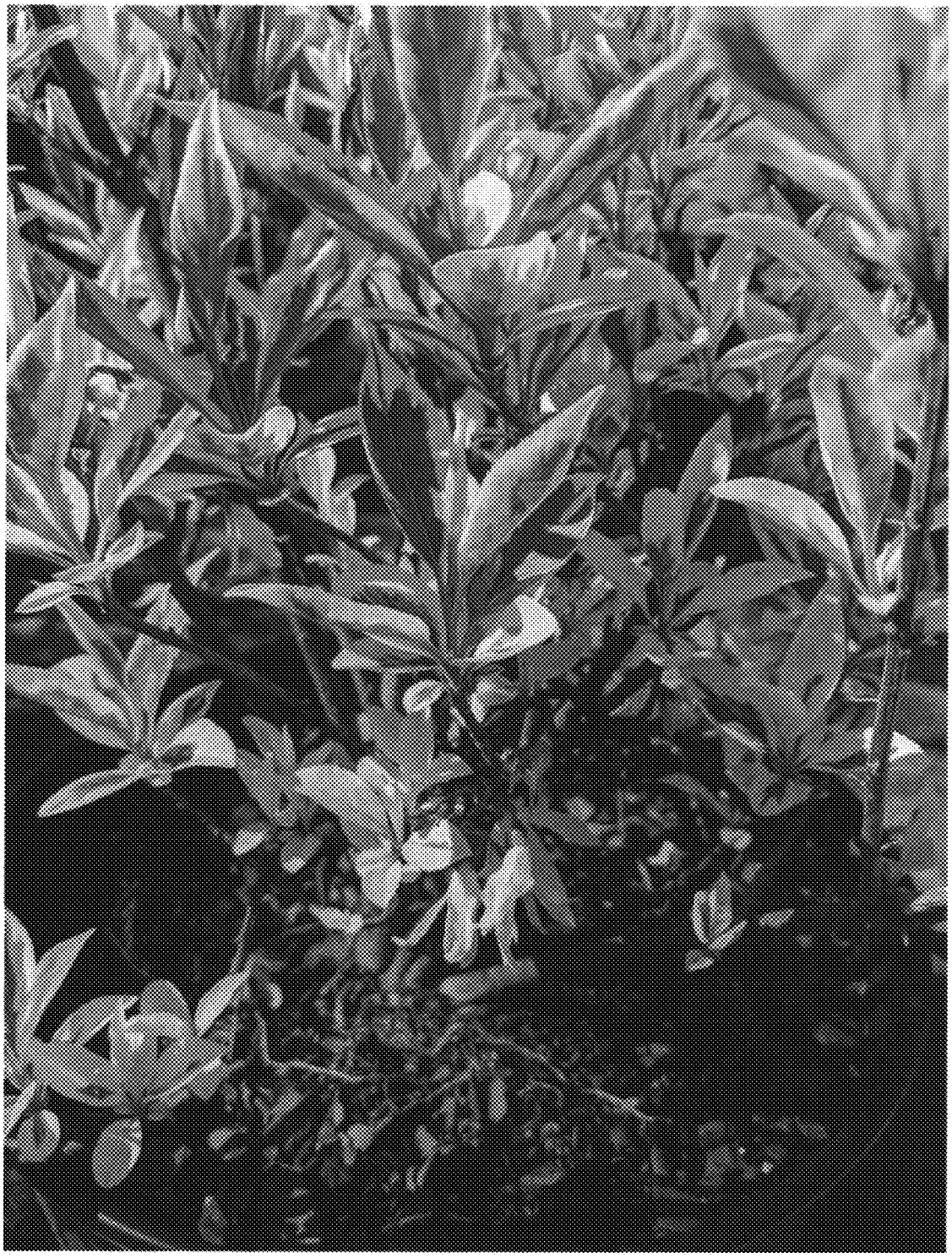
FIG. 4 shows flowering with flush of new foliage growth exhibiting solid yellow coloration and maturing foliage exhibiting the marginal leaf variegation.
Figure 5:
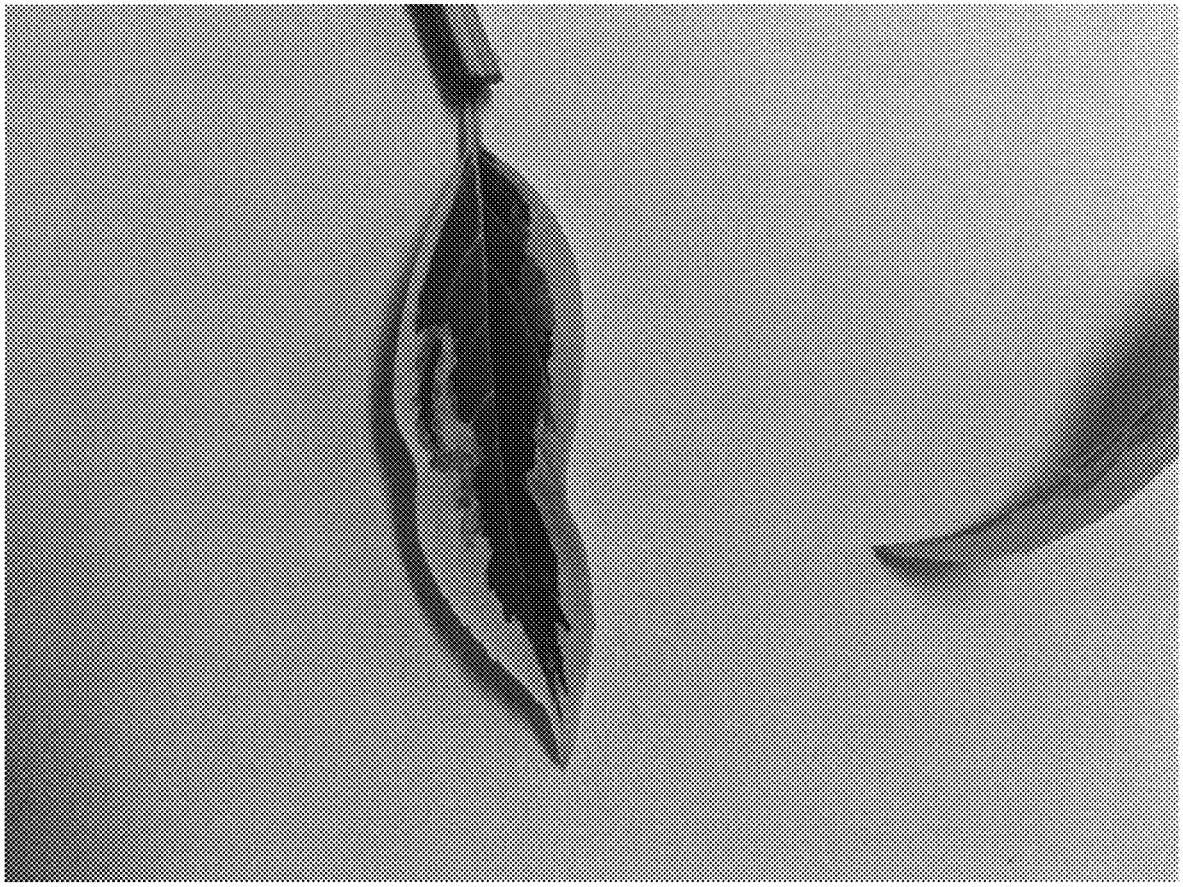
FIG. 5 shows a maturing leaf with the marginal leaf variegation.
Figure 6:
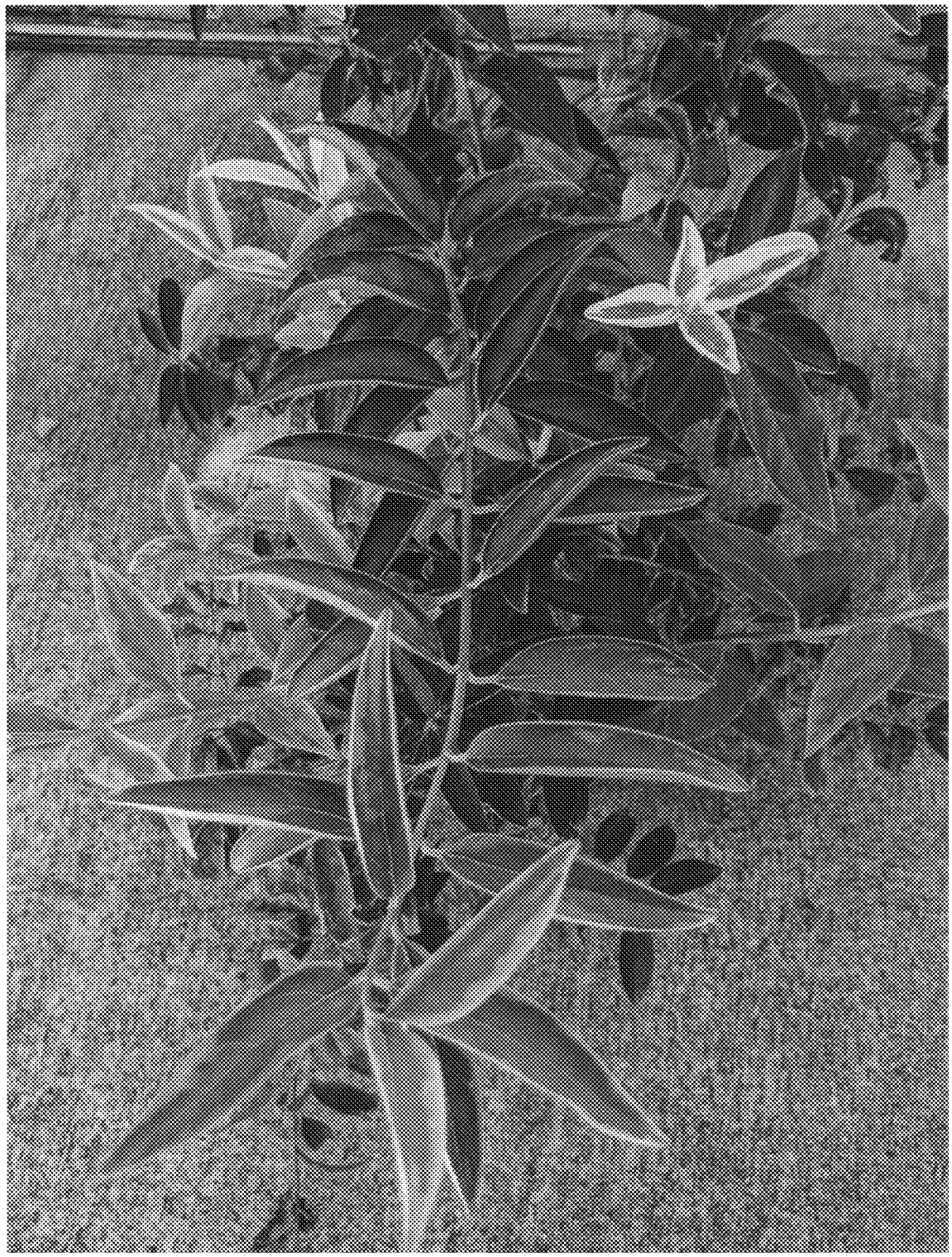
FIG. 6 shows a mature stem with the change from variegated foliage to green foliage over the course of time.
Figure 7:
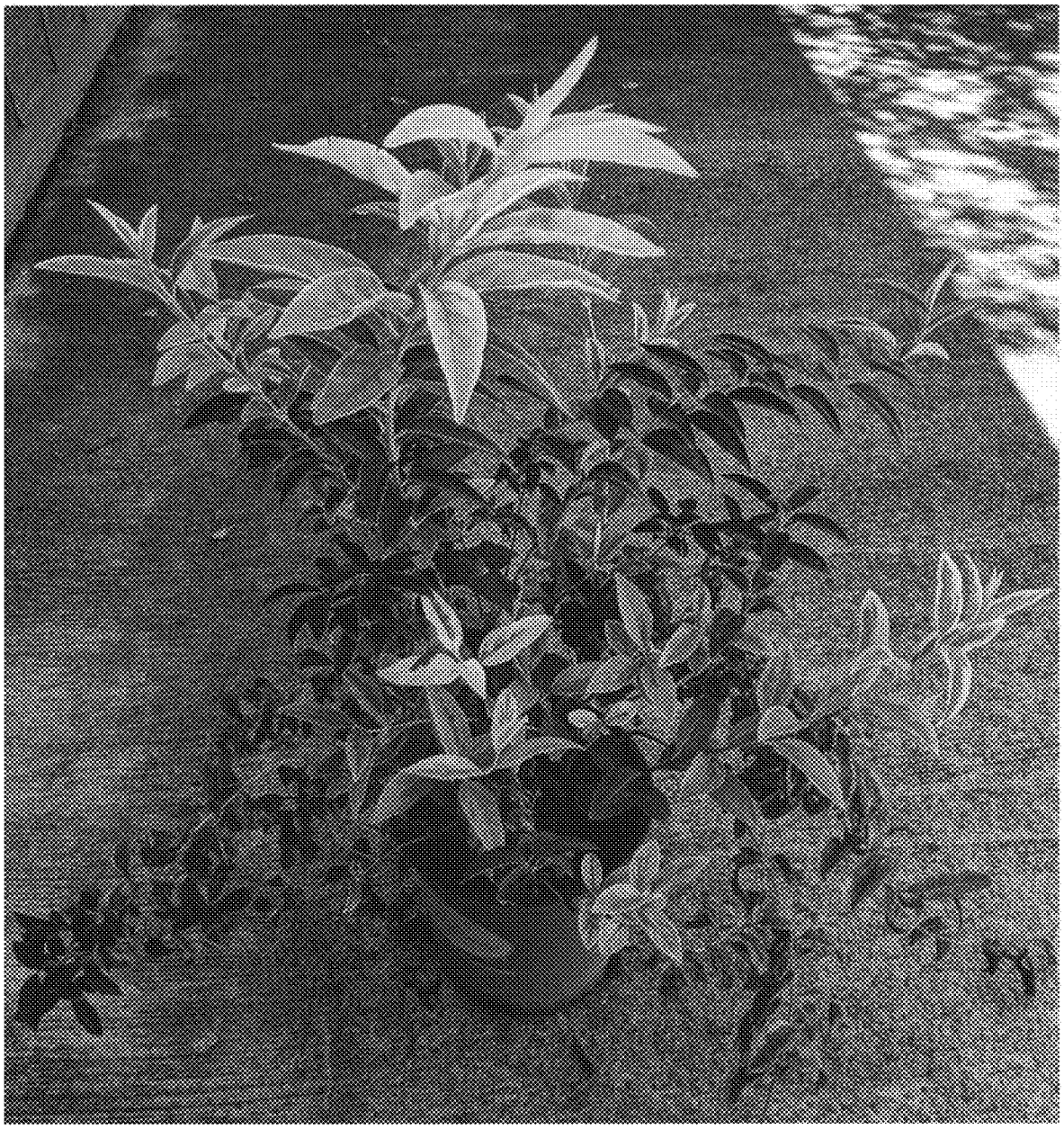
FIG. 7 shows overall plant habit and growth.

In the following description, color references are made to The Royal Horticultural Society Colour Chart, Sixth Edition, except where general terms of ordinary dictionary significance are used.

The following observations and measurements describe plants grown in 3 and 4-gallon containers under a natural photoperiod in full sun in Dearing, Ga. Detailed descriptions were taken in 2018 and 2019 from approximately 1-month-old plants, 3-year-old plants, 4-year-old plants, and 10-year-old plants grown from single vegetative stem cuttings. Measurements and numerical values represent averages of typical plant types when observed under artificial lighting.

DETAILED BOTANICAL DESCRIPTION

Classification:

*Family*.—Oleaceae.

Botanical: *Forsythia* x *intermedia*.

*Common*.—*Forsythia*.

*Denomination*.—'MNICH01'.

Propagation:

*Type*.—Semi-hardwood stem cuttings.

*Time to initiate roots*.—4 to 14 days when cuttings are taken from May to September.

*Time to produce a rooted young plant*.—12 weeks in a 38-cell liner tray.

Root description: Fibrous and freely branching.

Plant description:

*Plant type*.—Deciduous perennial shrub.

*Growth habit*.—Arching to erect.

*Branching habit*.—Long arching primary branches, freely branching on arch, suckers are produced from the base of the plant.

*Plant height*.—70.0 cm at 3 years of age, 130.0 cm at 10 years of age.

*Plant diameter*.—80.0 cm at 3 years of age, 150.0 cm at 10 years of age.

*Lateral branches*.—Length: Approximately 39.8 cm on a 1-year old branch. Diameter: Approximately 0.385 cm on a 1-year old branch. Internode length: Approximately 2.54 cm. Aspect: Lateral branches are 35 to 70 degrees from the primary branches. Texture: Glabrous on developing branches. Glabrous on developed branches with an overlay that exfoliates with age. Color: Developing branches: RHS 145A (yellow-green), turning to RHS N199C (grey-brown) at 1-year of growth, with a patchy overlay of RHS 198C (greyed-green) visible by the end of the first year's growth. Fully developed branches: RHS 197B (greyed-green) on a 3-year old branch, exfoliating overlay on mature branches are RHS 198C (greyed-green) after 3-years of growth.

Foliage description:

*Arrangement*.—Opposite.

*Blade*.—Length: Approximately 7.39 cm. Width: Approximately 2.38 cm. Shape: Simple involute leaf, lanceolate to narrowly ovate. Apex shape: Acute. Base shape: Cuneate. Margin: Mostly entire at base, occasionally upper two-thirds of margin is lightly serrate. Texture: Upper surface: Glabrous to glossy. Lower surface: Glabrous to semi-glossy. Venation pattern: Pinnate. Color: Developing leaves: Upper surface: Irregular margins of RHS 1A (green-yellow), center area along the mid-rib colored RHS 144A (yellow-green), with some leaves entirely colored RHS 1A (green-yellow) on the upper surface. Lowe surface: Irregular margins of RHS 1B (green-yellow), center area along the mid-rib colored RHS 144A (yellow-green), some leaves are entirely colored RHS 1B (green-yellow) on the lower surface. Fully developed leaves: Upper surface: Developed leaves are colored either entirely RHS 139A (green), RHS 139A (green) with a center coloring of RHS 138A (green), or RHS N138C (green) with a marginal coloring of RHS 145C (yellow-green), occasional sun scorching in the yellow-green regions can occur in June under full sun causing the leaves to burn and drop; venation is colored RHS 144C (yellow-green). Lower surface: Either entirely RHS N138B (green) or RHS N138C (green) with a marginal coloring of RHS 145C (yellow-green); venation is colored RHS 144D (yellow-green).

*Petiole*.—Length: Approximately 1.11 cm. Diameter: Approximately 0.2 cm. Texture (both upper and lower surfaces): Glabrous. Color (both upper and lower surfaces): RHS 145A (yellow-green).

Flower description:

*Appearance*.—Simple star shaped flower.

*Arrangement*.—One to three single flowers per node, occasionally up to 5 flowers have been observed per node.

*Habit*.—Held outward or downward from stem at nodes.

*Fragrance*.—None observed.

*Longevity*.—Ten days from bud swell under temperature highs ranging from 52 degrees F. to 70 degrees F., longevity may vary depending on weather conditions.

*Natural flowering season*.—February to March.

*Diameter*.—2.8 cm.

*Depth*.—1.8 cm.

*Bud*.—Length: 0.7 cm. Diameter: 0.2 cm. Shape: Oblanceolate. Color: Tight, immature buds are colored RHS 200B (brown) and turning RHS 143C (green) as buds mature and swell.

*Petals*.—Arrangement: Single whorl fused at the base. Quantity per flower: 4. Length: 1.5 cm, petals are fused 0.3 cm from the base. Width: 0.5 cm. Shape: Oblong, reflexed. Apex: Retuse, rounded. Base: Fused. Margin: Entire. Texture (both upper and lower surfaces): Glabrous. Color: When opening: Upper surface: RHS 7A (yellow) and RHS 8A (Yellow) with RHS 25A (orange) within the fused area at the base. Lower surface: RHS 7A (yellow) and RHS 8A (yellow). When fully opened: Upper surface: RHS 7A (yellow) and RHS 8A (yellow) with RHS 25A (orange) within the fused area at the base. Lower surface: RHS 7A (yellow) and RHS 8A (yellow).

*Sepals*.—Shape of calyx: Star shaped. Arrangement: Single whorl. Quantity per flower: 4. Length: 0.5 cm. Width: 0.2 cm. Shape: Obovate. Apex: Acute. Base: Fused. Margin: Entire. Texture: Smooth, slightly pubescent along the margin. Color: Outer surface colored RHS 143C (green) with areas of RHS N199C (grey-brown).

*Peduncles*.—Length: 0.6 cm. Diameter: 0.1 cm. Texture: Smooth. Angle: Curved downward. Color: RHS 164B (greyed-orange).

Reproductive organs:

*Stamens*.—Quantity per flower: 2. Anther: Length: 0.15 cm. Width: 0.1 cm. Shape: Ovate. Color: RHS 7A (yellow). Pollen: Amount: Abundant. Color: RHS 7A (yellow). Filament: Length: 0.2 cm. Color: RHS 8A (yellow).

*Pistils*.—Quantity per flower: 1. Length: 0.5 cm. Stigma: Shape: Lobed. Color: RHS 8A (yellow). Style: Length: 0.5 cm. Color: RHS 8A (yellow). Ovary color: RHS 145A (yellow-green).

Fruit and seed set: None observed.

Cold hardiness: Hardy to USDA zone 5, hardiness has been observed to be similar to 'Lynwood Gold' but has not been evaluated for additional cold hardiness.

Drought tolerance: Similar to the 'Lynwood Gold', has not been evaluated for additional drought tolerance.

Disease and insect resistance: Similar to the 'Lynwood Gold', has not been evaluated for additional disease and insect resistance.

COMPARISON WITH PARENTAL VARIETY

'MNICH01' differs from the parent plant 'Lynwood Gold' (unpatented) in that 'MNICH01' has a more reduced plant size of 130.0 cm in height and 150.0 cm in width, whereas plants of 'Lynwood Gold' are 244.0 cm in height and 244.0 cm in width. Additionally, new leaves of 'MNICH01' have a marginal variegation, whereas leaves of 'Lynwood Gold' are solid green with no marginal variegation.

COMPARISON WITH KNOWN CULTIVARS

'MNICH01' differs from the commercial *Forsythia* variety 'Kumson' (unpatented) in that leaves of 'MNICH01' have a marginal variegation, whereas leaves of 'Kumson' have a variegation over the entire leaf surface in a webbed pattern.

When 'MNICH01' is compared to the commercial *Forsythia* variety 'McKCitrine' (U.S. Plant Pat. No. 16,464, sold under the tradename "Citrus Swizzle"), 'MNICH01' has leaves with a more yellowish variegation with less serrated margins, and a larger plant size of 130.0 cm in height and 150.0 cm in width, whereas 'McKCitrine' has leaves with a more creamy variegation with greater serrated margins and a smaller plant size of 60.0 cm in height and 90.0 cm in width.

I claim:

1. A new and distinct variety of *Forsythia* plant named 'MNICH01', substantially as illustrated and described herein.

* * * * *